United States Patent [19]

Carl et al.

[11] Patent Number: 5,783,441
[45] Date of Patent: Jul. 21, 1998

[54] **GENE AND PROTEIN APPLICABLE TO THE PREPARATION OF VACCINES FOR *RICKETTSIA PROWAZEKII* AND *RICKETTSIA TYPHI* AND THE DETECTION OF BOTH**

[75] Inventors: Mitchell Carl, San Diego, Calif.; Michael E. Dobson, Rockville, Md.; Wei-Mei Ching, Bethesda, Md.; Gregory A. Dasch, Wheaton, Md.

[73] Assignee: The United States of America as represented by the Secretary of the Navy, Washington, D.C.

[21] Appl. No.: 169,927

[22] Filed: Dec. 20, 1993

Related U.S. Application Data

[63] Continuation-in-part of Ser. No. 742,128, Aug. 9, 1991, abandoned.

[51] Int. Cl.$^6$ ............................. C12N 15/00; C12N 1/20; A61K 39/00; C07H 21/02
[52] U.S. Cl. ......................... 435/320.1; 424/184.1; 424/185.1; 424/234.1; 435/252.3; 530/350; 536/23.1; 536/23.7
[58] Field of Search ..................... 424/184.1, 185.1, 424/234.1; 435/69.3, 172.1, 172.3, 252.3, 320.1, 252.33, 235.1, 254.2; 530/350, 825; 514/2; 536/23.1, 23.7

[56] References Cited

PUBLICATIONS

Gilmore, R.D. et al. Mol. Macrobio. 3(11) : 1575–1586 (1989).
Lee, C. C. et al. Science 239 : 1288–1291 (1988).
McDonald, G. et al. Science 235 : 83–85 (1987).
Krause, D.C. et al. Infect Imimun. 47(1) : 157–165 (1985).
Raonlt, D. et al. J. Immunol. Meth. 125:57–65 (1989).
Ellis, R.W. "New Technologies for Making Vaccines" In Vaccines Plotkin & Mortimer Eds., W.S. Saunders Co. (1988) pp. 568–575.
Boslego, J.W. et al. "Gonorrhea Vaccines" In Vaccines & Immunotherapy S.J. Cryz Ed., Pergrmon Press (1991) pp. 211–222.
Aniskovich, L.P. et al. Acta, Virol 35 :90–102 (1991)
Ching, W.M. et al. Ann. N.Y. Acad. Sci. 590: 334–351 (1990).

*Primary Examiner*—James C. Housel
*Assistant Examiner*—Jennifer Shaver
*Attorney, Agent, or Firm*—A. David Spevack; William C. Garvert

[57] ABSTRACT

All or part of the DNA sequence of the gene which encodes the S-layer protein of *R. prowazekii* as illustrated in Sequence ID No. 1 as well as a truncated identical piece of this gene in *R. typhi* as well as the 5' and 3' noncoding regions can be used for vaccination against typhus and spotted fever rickettsial infection or to diagnose the diseases caused by these bacteria. The invention is also accomplished by the deduced amino acid sequence of the S-layer protein of *R. prowazekii* derived from the DNA sequence of the encoding gene. Further, the invention includes the peptide or protein products based on all or parts of this gene.

2 Claims, 3 Drawing Sheets

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
( A ) LENGTH: 5319 base pairs
( B ) TYPE: nucleic acid
( C ) STRANDEDNESS: double
( D ) TOPOLOGY: circular ( i i ) MOLECULE TYPE: DNA (genomic)

( i i i ) HYPOTHETICAL: NO ( i v ) ANTI-SENSE: NO ( v ) FRAGMENT TYPE: internal ( v i ) ORIGINAL SOURCE:
( A ) ORGANISM: Rickettsia prowazekii
( B ) STRAIN: Breinl ( i x ) FEATURE:
( A ) NAME/KEY: -35_signal
( B ) LOCATION: 340..345

( i x ) FEATURE:
( A ) NAME/KEY: -10_signal
( B ) LOCATION: 363..368

( i x ) FEATURE:
( A ) NAME/KEY: CDS
( B ) LOCATION: 391..5226

( i x ) FEATURE:
( A ) NAME/KEY: RBS
( B ) LOCATION: 379..386

( i x ) FEATURE:
( A ) NAME/KEY: stem_loop
( B ) LOCATION: 5270..5306

( x ) PUBLICATION INFORMATION:
( A ) AUTHORS: Carl, M.
Dobson, M. E.
Ching, W. M.
Dasch, G. A.
( B ) TITLE: Characterization of the gene encoding the protective S- layer protein of Rickettsia prowazekii; presence of a truncated identical homolog in rickettsia typhi
( C ) JOURNAL: Proc. Natl. Acad. Sci. U.S.A.
( G ) DATE: 1990
( K ) RELEVANT RESIDUES IN SEQ ID NO:1: FROM 1 TO 5319

( x i ) SEQUENCE DESCRIPTION: SEQ ID NO:1:

TTAAGATACG TAATGACATA TGTAAAATTG ATATACAAAC TCATCATCGC AATAACTGAT 60

TATTATTTCA TAACACCAAT GTGATAAAAA TATAACATTT ATTAAAACTT TATAAAAAAA 120

```
CTACTGTGAT GCTTGTAATT ATGTACAATA TATAGTACAC TTAGCCCGTA GTTTAGAAAC        180

TATTGAAACA AAATATTAGG TTATTTCCTT ATCAAGTGTG GGATATCTTG ACCTCGTATT        240

TGATTAATTT GTTTTAATAC TAGATACTAA ATTTAACTTT AAATATAGGA AAAAATTATG       300

GCTCAAAAAC CATTTTCTAA AAAAATAATT TCCGCAGGAT TGGTAACTGC TTCCACGGCT        360

ACTATAGTAG CTGGTTTCTC TGGTGTAGCA ATG GGT GCT GCT ATG CAA TAT AAT        414
                                 Met Gly Ala Ala Met Gln Tyr Asn
                                  1               5

AGG ACA ACA AAT GCA GCA GCT ACA ACC TTT GAT GGT ATA GGC TTT GAT        462
Arg Thr Thr Asn Ala Ala Ala Thr Thr Phe Asp Gly Ile Gly Phe Asp
         10              15                  20

CAA GCT GCT GGT GCT AAT ATT CCT GTC GCT CCA AAT TCA GTT ATT ACT        510
Gln Ala Ala Gly Ala Asn Ile Pro Val Ala Pro Asn Ser Val Ile Thr
 25              30                  35                  40

GCT AAT GCT AAT AAT CCT ATT ACT TTT AAT ACT CCA AAC GGT CAT TTA        558
Ala Asn Ala Asn Asn Pro Ile Thr Phe Asn Thr Pro Asn Gly His Leu
                 45                  50                  55

AAT AGT TTA TTT TTG GAT ACG GCA AAT GAT TTA GCA GTA ACA ATT AAT        606
Asn Ser Leu Phe Leu Asp Thr Ala Asn Asp Leu Ala Val Thr Ile Asn
             60                  65                  70

GAG GAT ACT ACC TTA GGA TTT ATA ACA AAT ATT GCT CAG CAG GCT AAG        654
Glu Asp Thr Thr Leu Gly Phe Ile Thr Asn Ile Ala Gln Gln Ala Lys
         75                  80                  85

TTC TTT AAT TTT ACT GTT GCT GCT GGT AAA ATT CTT AAC ATA ACA GGG        702
Phe Phe Asn Phe Thr Val Ala Ala Gly Lys Ile Leu Asn Ile Thr Gly
     90                  95                  100

CAG GGT ATT ACT GTT CAA GAA GCT TCT AAT ACA ATA AAT GCT CAA AAT        750
Gln Gly Ile Thr Val Gln Glu Ala Ser Asn Thr Ile Asn Ala Gln Asn
105                 110                 115                 120

GCT CTT ACA AAA GTG CAT GGT GGC GCT GCT ATT AAC GCT AAT GAT CTT        798
Ala Leu Thr Lys Val His Gly Gly Ala Ala Ile Asn Ala Asn Asp Leu
             125                 130                 135

AGC GGG CTA GGA TCA ATA ACC TTT GCT GTG TGT CCT TCT GTA TTA GAA        846
Ser Gly Leu Gly Ser Ile Thr Phe Ala Val Cys Pro Ser Val Leu Glu
         140                 145                 150

TTT AAT TTA ATA AAT CCT ATC AAC TCA AGA AGC TCC TCT TAT CAC TTG        894
Phe Asn Leu Ile Asn Pro Ile Asn Ser Arg Ser Ser Ser Tyr His Leu
     155                 160                 165

GTG TCT AAT TCT AAA ATA GTT AAT GGT GGT AAT GGG ATA TTA AAT ATT        942
Val Ser Asn Ser Lys Ile Val Asn Gly Gly Asn Gly Ile Leu Asn Ile
170                 175                 180

ACT AAT GGA TTT ATT CAG GTT TCA GAT AAC ACT TTT GCT GGT ATT AAG        990
Thr Asn Gly Phe Ile Gln Val Ser Asp Asn Thr Phe Ala Gly Ile Lys
185                 190                 195                 200

ACC ATT AAT ATC GAT GAT TGT CAA GGT TTA ATG TTT AAT TCT ACT CCT       1038
Thr Ile Asn Ile Asp Asp Cys Gln Gly Leu Met Phe Asn Ser Thr Pro
             205                 210                 215

GAT GCC GCT AAT ACT TTA AAT TTA CAA GCA GGT GGT AAT ACT ATT AAT       1086
Asp Ala Ala Asn Thr Leu Asn Leu Gln Ala Gly Gly Asn Thr Ile Asn
         220                 225                 230

TTT AAT GGA ATA GAC GGT ACT GGT AAA TTA GTA TTA GTC AGT AAG AAT       1134
Phe Asn Gly Ile Asp Gly Thr Gly Lys Leu Val Leu Val Ser Lys Asn
     235                 240                 245

GGT GCT GCT ACC GAA TTT AAT GTT ACA GGA ACT TTA GGT GGT AAT CTA       1182
Gly Ala Ala Thr Glu Phe Asn Val Thr Gly Thr Leu Gly Gly Asn Leu
250                 255                 260

AAA GGT ATT ATT GAA TTG AAC ACT GCA GCA GTA GCT GGT AAA CTT ATC       1230
Lys Gly Ile Ile Glu Leu Asn Thr Ala Ala Val Ala Gly Lys Leu Ile
265                 270                 275                 280
```

```
                                                                    -continued TCT CTT GGA GGT GCT GCT AAT GCA GTA ATA GGT ACA GAT AAT GGA GCA         1278
Ser Leu Gly Gly Ala Ala Asn Ala Val Ile Gly Thr Asp Asn Gly Ala
            285                 290                 295

GGT AGA GCT GCA GGA TTT ATT GTT AGT GTT GAT AAT GGT AAT GCA GCA         1326
Gly Arg Ala Ala Gly Phe Ile Val Ser Val Asp Asn Gly Asn Ala Ala
            300                 305                 310

ACA ATT TCT GGA CAA GTT TAT GCT AAA AAC ATG GTG ATA CAA AGT GCT         1374
Thr Ile Ser Gly Gln Val Tyr Ala Lys Asn Met Val Ile Gln Ser Ala
            315                 320                 325

AAT GCA GGT GGA CAA GTC ACT TTT GAA CAC ATA GTT GAT GTT GGT TTA         1422
Asn Ala Gly Gly Gln Val Thr Phe Glu His Ile Val Asp Val Gly Leu
    330                 335                 340

GGC GGT ACC ACC AAC TTT AAA ACT GCA GAT TCT AAA GTT ATA ATA ACA         1470
Gly Gly Thr Thr Asn Phe Lys Thr Ala Asp Ser Lys Val Ile Ile Thr
345                 350                 355                 360

GAA AAC TCA AAC TTT GGT TCT ACT AAT TTT GGT AAT CTT GAC ACA CAG         1518
Glu Asn Ser Asn Phe Gly Ser Thr Asn Phe Gly Asn Leu Asp Thr Gln
                365                 370                 375

ATT GTA GTC CCT GAT ACT AAG ATT CTT AAA GGT AAC TTC ATA GGT GAT         1566
Ile Val Val Pro Asp Thr Lys Ile Leu Lys Gly Asn Phe Ile Gly Asp
            380                 385                 390

GTA AAA AAT AAC GGT AAT ACT GCA GGT GTG ATT ACT TTT AAT GCT AAT         1614
Val Lys Asn Asn Gly Asn Thr Ala Gly Val Ile Thr Phe Asn Ala Asn
        395                 400                 405

GGT GCT TTA GTA AGT GCT AGT ACT GAT CCA AAT ATT GCA GTA ACA AAT         1662
Gly Ala Leu Val Ser Ala Ser Thr Asp Pro Asn Ile Ala Val Thr Asn
    410                 415                 420

ATT AAT GCA ATT GAA GCA GAA GGG GCC GGG GTT GTA GAA TTA TCA GGA         1710
Ile Asn Ala Ile Glu Ala Glu Gly Ala Gly Val Val Glu Leu Ser Gly
425                 430                 435                 440

ATA CAT ATT GCA GAA TTA CGT TTA GGG AAT GGT GGC TCT ATC TTT AAA         1758
Ile His Ile Ala Glu Leu Arg Leu Gly Asn Gly Gly Ser Ile Phe Lys
                445                 450                 455

CTT GCT GAT GGC ACA GTA ATT AAT GGT CCA GTT AAC CAA AAT GCT CTT         1806
Leu Ala Asp Gly Thr Val Ile Asn Gly Pro Val Asn Gln Asn Ala Leu
            460                 465                 470

ATG AAT AAT AAT GCT CTT GCA GCT GGT TCT ATT CAG TTA GAT GGG AGT         1854
Met Asn Asn Asn Ala Leu Ala Ala Gly Ser Ile Gln Leu Asp Gly Ser
        475                 480                 485

GCT ATA ATT ACC GGT GAT ATA GGT AAC GGT GGT GTT AAT GCT GCG TTA         1902
Ala Ile Ile Thr Gly Asp Ile Gly Asn Gly Gly Val Asn Ala Ala Leu
    490                 495                 500

CAA CAC ATT ACT TTA GCT AAC GAT GCT TCA AAA ATA TTA GCA CTC GAT         1950
Gln His Ile Thr Leu Ala Asn Asp Ala Ser Lys Ile Leu Ala Leu Asp
505                 510                 515                 520

GGC GCA AAT ATT ATC GGG GCT AAT GTT GGT GGT GCA ATT CAT TTT CAA         1998
Gly Ala Asn Ile Ile Gly Ala Asn Val Gly Gly Ala Ile His Phe Gln
                525                 530                 535

GCT AAC GGT GGT ACT ATT AAA TTA ACA AAT ACT CAA AAT AAT ATT GTA         2046
Ala Asn Gly Gly Thr Ile Lys Leu Thr Asn Thr Gln Asn Asn Ile Val
            540                 545                 550

GTT AAT TTT GAT TTA GAT ATA ACT ACT GAT AAA ACA GGT GTT GTT GAT         2094
Val Asn Phe Asp Leu Asp Ile Thr Thr Asp Lys Thr Gly Val Val Asp
        555                 560                 565

GCA AGT AGT TTA ACA AAT AAT CAA ACT TTA ACT ATT AAT GGT AGT ATC         2142
Ala Ser Ser Leu Thr Asn Asn Gln Thr Leu Thr Ile Asn Gly Ser Ile
    570                 575                 580

GGT ACT GTT GTA GCT AAT ACT AAA ACA CTT GCA CAA TTA AAC ATC GGG         2190
Gly Thr Val Val Ala Asn Thr Lys Thr Leu Ala Gln Leu Asn Ile Gly
585                 590                 595                 600
```

| | | | | | | | | | | | | | | | | |
|---|---|---|---|---|---|---|---|---|---|---|---|---|---|---|---|---|
| TCA | AGT | AAA | ACA | ATA | TTA | AAT | GCT | GGC | GAT | GTC | GCT | ATT | AAC | GAG | TTA | 2238 |
| Ser | Ser | Lys | Thr | Ile | Leu | Asn | Ala | Gly | Asp | Val | Ala | Ile | Asn | Glu | Leu | |
| | | | | 605 | | | | 610 | | | | | | 615 | | |
| GTT | ATA | GAA | AAT | AAT | GGT | TCA | GTA | CAA | CTT | AAT | CAC | AAT | ACT | TAC | TTA | 2286 |
| Val | Ile | Glu | Asn | Asn | Gly | Ser | Val | Gln | Leu | Asn | His | Asn | Thr | Tyr | Leu | |
| | | | 620 | | | | | 625 | | | | | 630 | | | |
| ATA | ACA | AAA | ACT | ATC | AAT | GCT | GCA | AAC | CAA | GGT | CAA | ATA | ATC | GTT | GCC | 2334 |
| Ile | Thr | Lys | Thr | Ile | Asn | Ala | Ala | Asn | Gln | Gly | Gln | Ile | Ile | Val | Ala | |
| | | 635 | | | | | 640 | | | | | 645 | | | | |
| GCT | GAT | CCT | CTT | AAT | ACT | AAT | ACT | ACT | CTT | GCT | GAT | GGT | ACA | AAT | TTA | 2382 |
| Ala | Asp | Pro | Leu | Asn | Thr | Asn | Thr | Thr | Leu | Ala | Asp | Gly | Thr | Asn | Leu | |
| | 650 | | | | | 655 | | | | | 660 | | | | | |
| GGT | AGT | GCA | GAA | AAT | CCA | CTT | TCT | ACT | ATT | CAT | TTT | GCC | ACT | AAA | GCT | 2430 |
| Gly | Ser | Ala | Glu | Asn | Pro | Leu | Ser | Thr | Ile | His | Phe | Ala | Thr | Lys | Ala | |
| 665 | | | | | 670 | | | | | 675 | | | | | 680 | |
| GCT | AAT | GCT | GAC | TCT | ATA | TTA | AAT | GTA | GGT | AAA | GGA | GTA | AAT | TTA | TAT | 2478 |
| Ala | Asn | Ala | Asp | Ser | Ile | Leu | Asn | Val | Gly | Lys | Gly | Val | Asn | Leu | Tyr | |
| | | | | 685 | | | | | 690 | | | | | 695 | | |
| GCT | AAT | AAT | ATT | ACT | ACT | AAC | GAT | GCT | AAT | GTA | GGT | TCT | TTA | CAC | TTT | 2526 |
| Ala | Asn | Asn | Ile | Thr | Thr | Asn | Asp | Ala | Asn | Val | Gly | Ser | Leu | His | Phe | |
| | | | 700 | | | | | 705 | | | | | 710 | | | |
| AGG | TCT | GGT | GGT | ACA | AGT | ATA | GTA | AGT | GGT | ACA | GTT | GGT | GGA | CAG | CAA | 2574 |
| Arg | Ser | Gly | Gly | Thr | Ser | Ile | Val | Ser | Gly | Thr | Val | Gly | Gly | Gln | Gln | |
| | | 715 | | | | | 720 | | | | | 725 | | | | |
| GGT | CAT | AAG | CTT | AAT | AAT | TTA | ATA | TTA | GAT | AAT | GGT | ACT | ACT | GTT | AAG | 2622 |
| Gly | His | Lys | Leu | Asn | Asn | Leu | Ile | Leu | Asp | Asn | Gly | Thr | Thr | Val | Lys | |
| | 730 | | | | | 735 | | | | | 740 | | | | | |
| TTT | TTA | GGT | GAT | ACA | ACA | TTT | AAT | GGT | GGT | ACT | AAA | ATT | GAA | GGT | AAA | 2670 |
| Phe | Leu | Gly | Asp | Thr | Thr | Phe | Asn | Gly | Gly | Thr | Lys | Ile | Glu | Gly | Lys | |
| 745 | | | | | 750 | | | | | 755 | | | | | 760 | |
| TCC | ATC | TTG | CAA | ATT | AGC | AAT | AAT | TAT | ACT | ACT | GAT | CAT | GTT | GAA | TCT | 2718 |
| Ser | Ile | Leu | Gln | Ile | Ser | Asn | Asn | Tyr | Thr | Thr | Asp | His | Val | Glu | Ser | |
| | | | | 765 | | | | | 770 | | | | | 775 | | |
| GCT | GAT | AAT | ACT | GGT | ACA | TTA | GAA | TTT | GTT | AAC | ACT | GAT | CCT | ATA | ACC | 2766 |
| Ala | Asp | Asn | Thr | Gly | Thr | Leu | Glu | Phe | Val | Asn | Thr | Asp | Pro | Ile | Thr | |
| | | | 780 | | | | | 785 | | | | | 790 | | | |
| GTA | ACA | TTA | AAT | AAA | CAA | GGT | GCT | TAT | TTT | GGT | GTT | TTA | AAA | CAA | GTA | 2814 |
| Val | Thr | Leu | Asn | Lys | Gln | Gly | Ala | Tyr | Phe | Gly | Val | Leu | Lys | Gln | Val | |
| | | 795 | | | | | 800 | | | | | 805 | | | | |
| ATT | ATT | TCT | GGT | CCA | GGT | AAC | ATA | GTA | TTT | AAT | GAG | ATA | GGT | AAT | GTA | 2862 |
| Ile | Ile | Ser | Gly | Pro | Gly | Asn | Ile | Val | Phe | Asn | Glu | Ile | Gly | Asn | Val | |
| | 810 | | | | | 815 | | | | | 820 | | | | | |
| GGA | ATT | GTA | CAT | GGT | ATA | GCA | GCT | AAT | TCA | ATT | TCT | TTT | GAA | AAT | GCA | 2910 |
| Gly | Ile | Val | His | Gly | Ile | Ala | Ala | Asn | Ser | Ile | Ser | Phe | Glu | Asn | Ala | |
| 825 | | | | | 830 | | | | | 835 | | | | | 840 | |
| AGT | TTA | GGT | ACA | TCT | TTA | TTC | TTA | CCT | AGT | GGT | ACT | CCA | TTA | GAT | GTT | 2958 |
| Ser | Leu | Gly | Thr | Ser | Leu | Phe | Leu | Pro | Ser | Gly | Thr | Pro | Leu | Asp | Val | |
| | | | | 845 | | | | | 850 | | | | | 855 | | |
| TTA | ACA | ATT | AAA | AGT | ACC | GTA | GGT | AAT | GGT | ACA | GTA | GAT | AAT | TTT | AAT | 3006 |
| Leu | Thr | Ile | Lys | Ser | Thr | Val | Gly | Asn | Gly | Thr | Val | Asp | Asn | Phe | Asn | |
| | | | 860 | | | | | 865 | | | | | 870 | | | |
| GCT | CCT | ATT | GTA | GTT | GTA | TCA | GGT | ATT | GAT | AGT | ATG | ATC | AAT | AAC | GGT | 3054 |
| Ala | Pro | Ile | Val | Val | Val | Ser | Gly | Ile | Asp | Ser | Met | Ile | Asn | Asn | Gly | |
| | | 875 | | | | | 880 | | | | | 885 | | | | |
| CAA | ATC | ATC | GGT | GAT | AAA | AAG | AAT | ATT | ATA | GCT | CTA | TCG | CTT | GGA | AGT | 3102 |
| Gln | Ile | Ile | Gly | Asp | Lys | Lys | Asn | Ile | Ile | Ala | Leu | Ser | Leu | Gly | Ser | |
| | | | 890 | | | | | 895 | | | | | 900 | | | |
| GAT | AAC | AGT | ATT | ACT | GTT | AAT | GCT | AAT | ACA | TTA | TAT | TCA | GGT | ATC | AGA | 3150 |
| Asp | Asn | Ser | Ile | Thr | Val | Asn | Ala | Asn | Thr | Leu | Tyr | Ser | Gly | Ile | Arg | |
| 905 | | | | | 910 | | | | | 915 | | | | | 920 | |

| | | | | | | | | | | | | | | | | |
|---|---|---|---|---|---|---|---|---|---|---|---|---|---|---|---|---|
| ACT | ACA | AAA | AAT | AAT | CAA | GGT | ACT | GTG | ACA | CTT | AGT | GGT | GGT | ATG | CCT | 3198 |
| Thr | Thr | Lys | Asn | Asn | Gln | Gly | Thr | Val | Thr | Leu | Ser | Gly | Gly | Met | Pro | |
| | | | | 925 | | | | 930 | | | | | | 935 | | |
| AAT | AAT | CCT | GGT | ACA | ATT | TAT | GGT | TTA | GGT | TTA | GAG | AAT | GGT | AGT | CCA | 3246 |
| Asn | Asn | Pro | Gly | Thr | Ile | Tyr | Gly | Leu | Gly | Leu | Glu | Asn | Gly | Ser | Pro | |
| | | | 940 | | | | | 945 | | | | | 950 | | | |
| AAG | TTA | AAA | CAA | GTG | ACA | TTT | ACT | ACA | GAT | TAT | AAC | AAC | TTA | GGT | AGT | 3294 |
| Lys | Leu | Lys | Gln | Val | Thr | Phe | Thr | Thr | Asp | Tyr | Asn | Asn | Leu | Gly | Ser | |
| | | 955 | | | | | | 960 | | | | | 965 | | | |
| ATT | ATT | GCA | AAT | AAT | GTA | ACA | ATT | AAT | GAT | GAT | GTA | ACT | CTT | ACT | ACA | 3342 |
| Ile | Ile | Ala | Asn | Asn | Val | Thr | Ile | Asn | Asp | Asp | Val | Thr | Leu | Thr | Thr | |
| | | 970 | | | | | 975 | | | | | 980 | | | | |
| GGA | GGT | ATA | GCA | GGG | ACA | GAT | TTT | GAC | GCT | AAA | ATT | ACT | CTT | GGA | AGT | 3390 |
| Gly | Gly | Ile | Ala | Gly | Thr | Asp | Phe | Asp | Ala | Lys | Ile | Thr | Leu | Gly | Ser | |
| 985 | | | | | 990 | | | | | 995 | | | | | 1000 | |
| GTT | AAC | GGT | AAC | GCT | AAC | GTA | AGG | TTT | GTT | GAT | AGT | ACA | TTT | TCT | GAT | 3438 |
| Val | Asn | Gly | Asn | Ala | Asn | Val | Arg | Phe | Val | Asp | Ser | Thr | Phe | Ser | Asp | |
| | | | | | 1005 | | | | | 1010 | | | | | 1015 | |
| CCT | AGA | AGT | ATG | ATT | GTT | GCT | ACT | CAA | GCT | AAT | AAG | GGT | ACT | GTA | ACT | 3486 |
| Pro | Arg | Ser | Met | Ile | Val | Ala | Thr | Gln | Ala | Asn | Lys | Gly | Thr | Val | Thr | |
| | | | 1020 | | | | | 1025 | | | | | 1030 | | | |
| TAT | TTA | GGT | AAT | GCA | TTA | GTT | AGT | AAT | ATC | GGT | AGT | TTA | GAT | ACT | CCT | 3534 |
| Tyr | Leu | Gly | Asn | Ala | Leu | Val | Ser | Asn | Ile | Gly | Ser | Leu | Asp | Thr | Pro | |
| | | | 1035 | | | | | 1040 | | | | | 1045 | | | |
| GTA | GCT | TCT | GTT | AGA | TTT | ACA | GGT | AAT | GAT | AGT | GGG | GCA | GGA | TTA | CAA | 3582 |
| Val | Ala | Ser | Val | Arg | Phe | Thr | Gly | Asn | Asp | Ser | Gly | Ala | Gly | Leu | Gln | |
| | 1050 | | | | | 1055 | | | | | 1060 | | | | | |
| GGC | AAT | ATT | TAT | TCA | CAA | AAT | ATA | GAT | TTT | GGT | ACT | TAT | AAT | TTA | ACT | 3630 |
| Gly | Asn | Ile | Tyr | Ser | Gln | Asn | Ile | Asp | Phe | Gly | Thr | Tyr | Asn | Leu | Thr | |
| 1065 | | | | | 1070 | | | | | 1075 | | | | | 1080 | |
| ATT | CTA | AAT | TCT | AAT | GTC | ATT | TTA | GGT | GGT | GGT | ACT | ACT | GCT | ATT | AAT | 3678 |
| Ile | Leu | Asn | Ser | Asn | Val | Ile | Leu | Gly | Gly | Gly | Thr | Thr | Ala | Ile | Asn | |
| | | | | 1085 | | | | | 1090 | | | | | 1095 | | |
| GGT | GAA | ATC | GAT | CTT | CTG | ACA | AAT | AAT | TTA | ATA | TTT | GCA | AAT | GGT | ACT | 3726 |
| Gly | Glu | Ile | Asp | Leu | Leu | Thr | Asn | Asn | Leu | Ile | Phe | Ala | Asn | Gly | Thr | |
| | | | 1100 | | | | | 1105 | | | | | 1110 | | | |
| TCA | ACA | TGG | GGT | GAT | AAT | ACT | TCT | ATT | AGT | ACA | ACG | TTA | AAT | GTA | TCA | 3774 |
| Ser | Thr | Trp | Gly | Asp | Asn | Thr | Ser | Ile | Ser | Thr | Thr | Leu | Asn | Val | Ser | |
| | | | 1115 | | | | | 1120 | | | | | 1125 | | | |
| AGC | GGT | AAT | ATA | GGT | CAA | GTA | GTC | ATT | GCC | GAA | GAT | GCT | CAA | GTT | AAC | 3822 |
| Ser | Gly | Asn | Ile | Gly | Gln | Val | Val | Ile | Ala | Glu | Asp | Ala | Gln | Val | Asn | |
| | | | 1130 | | | | | 1135 | | | | | 1140 | | | |
| GCA | ACA | ACT | ACA | GGA | ACT | ACA | ACC | ATT | AAA | ATA | CAA | GAT | AAT | GCT | AAT | 3870 |
| Ala | Thr | Thr | Thr | Gly | Thr | Thr | Thr | Ile | Lys | Ile | Gln | Asp | Asn | Ala | Asn | |
| 1145 | | | | | 1150 | | | | | 1155 | | | | | 1160 | |
| GCA | AAT | TTC | AGT | GGC | ACA | CAA | GCT | TAT | ACT | TTA | ATT | CAA | GGT | GGT | GCT | 3918 |
| Ala | Asn | Phe | Ser | Gly | Thr | Gln | Ala | Tyr | Thr | Leu | Ile | Gln | Gly | Gly | Ala | |
| | | | | 1165 | | | | | 1170 | | | | | 1175 | | |
| AGA | TTT | AAT | GGT | ACT | TTA | GGA | GCT | CCT | AAC | TTT | GCT | GTA | ACA | GGA | AGT | 3966 |
| Arg | Phe | Asn | Gly | Thr | Leu | Gly | Ala | Pro | Asn | Phe | Ala | Val | Thr | Gly | Ser | |
| | | | 1180 | | | | | 1185 | | | | | 1190 | | | |
| AAT | ATT | TTC | GTA | AAA | TAT | GAA | CTA | ATA | CGT | GAT | TCT | AAC | CAG | GAT | TAT | 4014 |
| Asn | Ile | Phe | Val | Lys | Tyr | Glu | Leu | Ile | Arg | Asp | Ser | Asn | Gln | Asp | Tyr | |
| | | | 1195 | | | | | 1200 | | | | | 1205 | | | |
| GTA | TTA | ACA | CGT | ACT | AAC | GAT | GTA | TTA | AAC | GTA | GTT | ACA | ACA | GCT | GTT | 4062 |
| Val | Leu | Thr | Arg | Thr | Asn | Asp | Val | Leu | Asn | Val | Val | Thr | Thr | Ala | Val | |
| | | 1210 | | | | | 1215 | | | | | 1220 | | | | |
| GGA | AAT | AGT | GCA | ATT | GCA | AAT | GCA | CCT | GGT | GTA | AGT | CAG | AAC | ATT | TCT | 4110 |
| Gly | Asn | Ser | Ala | Ile | Ala | Asn | Ala | Pro | Gly | Val | Ser | Gln | Asn | Ile | Ser | |
| 1225 | | | | | 1230 | | | | | 1235 | | | | | 1240 | |

| | | | | | | | | | | | | | | | | |
|---|---|---|---|---|---|---|---|---|---|---|---|---|---|---|---|---|
| AGA | TGC | TTA | GAA | TCA | ACA | AAT | ACA | GCA | GCT | TAT | AAT | AAT | ATG | CTT | TTA | 4158 |
| Arg | Cys | Leu | Glu | Ser | Thr | Asn | Thr | Ala | Ala | Tyr | Asn | Asn | Met | Leu | Leu | |
| | | | 1245 | | | | | 1250 | | | | | | 1255 | | |
| GCT | AAA | GAT | CCT | TCT | GAT | GTT | GCA | ACA | TTT | GTA | GGA | GCT | ATT | GCT | ACA | 4206 |
| Ala | Lys | Asp | Pro | Ser | Asp | Val | Ala | Thr | Phe | Val | Gly | Ala | Ile | Ala | Thr | |
| | | | 1260 | | | | | 1265 | | | | | 1270 | | | |
| GAT | ACA | AGT | GCG | GCT | GTA | ACT | ACA | GTA | AAC | TTA | AAT | GAT | ACA | CAA | AAA | 4254 |
| Asp | Thr | Ser | Ala | Ala | Val | Thr | Thr | Val | Asn | Leu | Asn | Asp | Thr | Gln | Lys | |
| | | 1275 | | | | | 1280 | | | | | 1285 | | | | |
| ACT | CAA | GAT | CTA | CTT | AGT | AAT | AGG | CTA | GGT | ACA | CTT | AGA | TAT | CTA | AGT | 4302 |
| Thr | Gln | Asp | Leu | Leu | Ser | Asn | Arg | Leu | Gly | Thr | Leu | Arg | Tyr | Leu | Ser | |
| | | 1290 | | | | 1295 | | | | | 1300 | | | | | |
| AAT | GCT | GAA | ACT | TCT | GAT | GTT | GCT | GGA | TCT | GCA | ACA | GGT | GCA | GTG | TCT | 4350 |
| Asn | Ala | Glu | Thr | Ser | Asp | Val | Ala | Gly | Ser | Ala | Thr | Gly | Ala | Val | Ser | |
| 1305 | | | | | 1310 | | | | | 1315 | | | | | 1320 | |
| TCA | GGT | GAT | GAA | GCG | GAA | GTA | TCT | TAT | GGT | GTA | TGG | GCT | AAA | CCT | TTC | 4398 |
| Ser | Gly | Asp | Glu | Ala | Glu | Val | Ser | Tyr | Gly | Val | Trp | Ala | Lys | Pro | Phe | |
| | | | | 1325 | | | | | 1330 | | | | | 1335 | | |
| TAT | AAC | ATT | GCA | GAA | CAA | GAC | AAA | AAA | GGT | GGT | ATA | GCT | GGT | TAT | AAA | 4446 |
| Tyr | Asn | Ile | Ala | Glu | Gln | Asp | Lys | Lys | Gly | Gly | Ile | Ala | Gly | Tyr | Lys | |
| | | | 1340 | | | | | 1345 | | | | | 1350 | | | |
| GCA | AAA | ACT | ACT | GGG | GTT | GTA | GTT | GGT | TTA | GAT | ACT | CTC | GCT | AGC | GAT | 4494 |
| Ala | Lys | Thr | Thr | Gly | Val | Val | Val | Gly | Leu | Asp | Thr | Leu | Ala | Ser | Asp | |
| | | 1355 | | | | | 1360 | | | | | 1365 | | | | |
| AAC | CTA | ATG | ATT | GGG | GCA | GCT | ATT | GGG | ATC | ACT | AAA | ACT | GAT | ATA | AAA | 4542 |
| Asn | Leu | Met | Ile | Gly | Ala | Ala | Ile | Gly | Ile | Thr | Lys | Thr | Asp | Ile | Lys | |
| | | 1370 | | | | | 1375 | | | | | 1380 | | | | |
| CAC | CAA | GAT | TAT | AAG | AAA | GGT | GAT | AAA | ACT | GAT | ATT | AAT | GGT | TTA | TCA | 4590 |
| His | Gln | Asp | Tyr | Lys | Lys | Gly | Asp | Lys | Thr | Asp | Ile | Asn | Gly | Leu | Ser | |
| 1385 | | | | 1390 | | | | | 1395 | | | | | 1400 | | |
| TTC | TCT | CTA | TAT | GGT | TCC | CAA | CAG | CTT | GTT | AAG | AAT | TTC | TTT | GCT | CAA | 4638 |
| Phe | Ser | Leu | Tyr | Gly | Ser | Gln | Gln | Leu | Val | Lys | Asn | Phe | Phe | Ala | Gln | |
| | | | | 1405 | | | | | 1410 | | | | | 1415 | | |
| GGT | AAT | TCA | ATC | TTT | ACC | TTA | AAC | AAA | GTC | AAA | AGT | AAA | AGT | CAG | CGT | 4686 |
| Gly | Asn | Ser | Ile | Phe | Thr | Leu | Asn | Lys | Val | Lys | Ser | Lys | Ser | Gln | Arg | |
| | | | 1420 | | | | | 1425 | | | | | 1430 | | | |
| TAC | TTC | TTC | GAG | TCT | AAT | GGT | AAG | ATG | AGC | AAG | CAA | ATT | GCT | GCT | GGT | 4734 |
| Tyr | Phe | Phe | Glu | Ser | Asn | Gly | Lys | Met | Ser | Lys | Gln | Ile | Ala | Ala | Gly | |
| | | | 1435 | | | | | 1440 | | | | | 1445 | | | |
| AAT | TAC | GAT | AAC | ATG | ACA | TTT | GGT | GGT | AAT | TTA | ATA | TTT | GGT | TAT | GAT | 4782 |
| Asn | Tyr | Asp | Asn | Met | Thr | Phe | Gly | Gly | Asn | Leu | Ile | Phe | Gly | Tyr | Asp | |
| | | | 1450 | | | | | 1455 | | | | | 1460 | | | |
| TAT | AAT | GCA | ATG | CCA | AAT | GTA | TTA | GTA | ACT | CCA | ATG | GCA | GGA | CTT | AGC | 4830 |
| Tyr | Asn | Ala | Met | Pro | Asn | Val | Leu | Val | Thr | Pro | Met | Ala | Gly | Leu | Ser | |
| 1465 | | | | | 1470 | | | | | 1475 | | | | | 1480 | |
| TAC | TTA | AAA | TCT | TCT | AAT | GAA | AAT | TAT | AAA | GAA | ACC | GGT | ACA | ACA | GTT | 4878 |
| Tyr | Leu | Lys | Ser | Ser | Asn | Glu | Asn | Tyr | Lys | Glu | Thr | Gly | Thr | Thr | Val | |
| | | | | 1485 | | | | | 1490 | | | | | 1495 | | |
| GCA | AAT | AAG | CGC | ATT | AAT | AGC | AAA | TTT | AGT | GAT | AGA | GTC | GAT | TTA | ATA | 4926 |
| Ala | Asn | Lys | Arg | Ile | Asn | Ser | Lys | Phe | Ser | Asp | Arg | Val | Asp | Leu | Ile | |
| | | | | 1500 | | | | | 1505 | | | | | 1510 | | |
| GTA | GGG | GCT | AAA | GTA | GCT | GGT | AGT | ACT | GTG | AAT | ATA | ACT | GAT | ATT | GTG | 4974 |
| Val | Gly | Ala | Lys | Val | Ala | Gly | Ser | Thr | Val | Asn | Ile | Thr | Asp | Ile | Val | |
| | | | 1515 | | | | | 1520 | | | | | 1525 | | | |
| ATA | TAT | CCG | GAA | ATT | CAT | TCT | TTT | GTG | GTG | CAC | AAA | GTA | AAT | GGT | AAA | 5022 |
| Ile | Tyr | Pro | Glu | Ile | His | Ser | Phe | Val | Val | His | Lys | Val | Asn | Gly | Lys | |
| | | | | 1530 | | | | | 1535 | | | | | 1540 | | |
| TTA | TCT | AAC | TCT | CAG | TCT | ATG | TTA | GAT | GGA | CAA | ACT | GCT | CCA | TTT | ATC | 5070 |
| Leu | Ser | Asn | Ser | Gln | Ser | Met | Leu | Asp | Gly | Gln | Thr | Ala | Pro | Phe | Ile | |
| 1545 | | | | | 1550 | | | | | 1555 | | | | | 1560 | |

```
AGT CAA CCT GAT AGA ACT GCT AAA ACG TCT TAT AAT ATA GGC TTA AGT        5118
Ser Gln Pro Asp Arg Thr Ala Lys Thr Ser Tyr Asn Ile Gly Leu Ser
            1565                1570                1575

GCA AAC ATA AAA TCT GAT GCT AAG ATG GAG TAT GGT ATC GGT TAT GAT        5166
Ala Asn Ile Lys Ser Asp Ala Lys Met Glu Tyr Gly Ile Gly Tyr Asp
        1580                1585                1590

TTT AAT TCT GCA AGT AAA TAT ACT GCA CAT CAA GGT ACT TTA AAA GTA        5214
Phe Asn Ser Ala Ser Lys Tyr Thr Ala His Gln Gly Thr Leu Lys Val
        1595                1600                1605

CGT GTA AAC TTC TAATAATTAT TTGTGATTTT AGTAAGTTTA TAACTTGATT            5266
Arg Val Asn Phe
        1610

AAGAAAAAAA GCCCACTTTG AAAAAATGGG CTTTTTTTCT AGTTATGTAA TAA             5319
```

( 2 ) INFORMATION FOR SEQ ID NO:2:

( i ) SEQUENCE CHARACTERISTICS:
( A ) LENGTH: 1612 amino acids
( B ) TYPE: amino acid
( D ) TOPOLOGY: linear ( i i ) MOLECULE TYPE: protein ( x i ) SEQUENCE DESCRIPTION: SEQ ID NO:2:

```
Met Gly Ala Ala Met Gln Tyr Asn Arg Thr Thr Asn Ala Ala Ala Thr
  1               5                  10                  15

Thr Phe Asp Gly Ile Gly Phe Asp Gln Ala Ala Gly Ala Asn Ile Pro
             20                  25                  30

Val Ala Pro Asn Ser Val Ile Thr Ala Asn Ala Asn Asn Pro Ile Thr
         35                  40                  45

Phe Asn Thr Pro Asn Gly His Leu Asn Ser Leu Phe Leu Asp Thr Ala
 50                  55                  60

Asn Asp Leu Ala Val Thr Ile Asn Glu Asp Thr Thr Leu Gly Phe Ile
 65                  70                  75                  80

Thr Asn Ile Ala Gln Gln Ala Lys Phe Phe Asn Phe Thr Val Ala Ala
                 85                  90                  95

Gly Lys Ile Leu Asn Ile Thr Gly Gln Gly Ile Thr Val Gln Glu Ala
                100                 105                 110

Ser Asn Thr Ile Asn Ala Gln Asn Ala Leu Thr Lys Val His Gly Gly
             115                 120                 125

Ala Ala Ile Ala Asn Asp Leu Ser Gly Leu Gly Ser Ile Thr Phe
130                 135                 140

Ala Val Cys Pro Ser Val Leu Glu Phe Asn Leu Ile Asn Pro Ile Asn
145                 150                 155                 160

Ser Arg Ser Ser Tyr His Leu Val Ser Asn Ser Lys Ile Val Asn
                165                 170                 175

Gly Gly Asn Gly Ile Leu Asn Ile Thr Asn Gly Phe Ile Gln Val Ser
             180                 185                 190

Asp Asn Thr Phe Ala Gly Ile Lys Thr Ile Asn Ile Asp Asp Cys Gln
         195                 200                 205

Gly Leu Met Phe Asn Ser Thr Pro Asp Ala Ala Asn Thr Leu Asn Leu
210                 215                 220

Gln Ala Gly Gly Asn Thr Ile Asn Phe Asn Gly Ile Asp Gly Thr Gly
225                 230                 235                 240

Lys Leu Val Leu Val Ser Lys Asn Gly Ala Ala Thr Glu Phe Asn Val
                245                 250                 255

Thr Gly Thr Leu Gly Gly Asn Leu Lys Gly Ile Ile Glu Leu Asn Thr
             260                 265                 270
```

```
Ala  Ala  Val  Ala  Gly  Lys  Leu  Ile  Ser  Leu  Gly  Gly  Ala  Ala  Asn  Ala
          275                 280                 285

Val  Ile  Gly  Thr  Asp  Asn  Gly  Ala  Gly  Arg  Ala  Ala  Gly  Phe  Ile  Val
     290                 295                 300

Ser  Val  Asp  Asn  Gly  Asn  Ala  Ala  Thr  Ile  Ser  Gly  Gln  Val  Tyr  Ala
305                      310                 315                      320

Lys  Asn  Met  Val  Ile  Gln  Ser  Ala  Asn  Ala  Gly  Gly  Gln  Val  Thr  Phe
               325                      330                      335

Glu  His  Ile  Val  Asp  Val  Gly  Leu  Gly  Gly  Thr  Thr  Asn  Phe  Lys  Thr
               340                 345                      350

Ala  Asp  Ser  Lys  Val  Ile  Ile  Thr  Glu  Asn  Ser  Asn  Phe  Gly  Ser  Thr
          355                 360                      365

Asn  Phe  Gly  Asn  Leu  Asp  Thr  Gln  Ile  Val  Val  Pro  Asp  Thr  Lys  Ile
370                      375                      380

Leu  Lys  Gly  Asn  Phe  Ile  Gly  Asp  Val  Lys  Asn  Asn  Gly  Asn  Thr  Ala
385                 390                      395                      400

Gly  Val  Ile  Thr  Phe  Asn  Ala  Asn  Gly  Ala  Leu  Val  Ser  Ala  Ser  Thr
               405                      410                      415

Asp  Pro  Asn  Ile  Ala  Val  Thr  Asn  Ile  Asn  Ala  Ile  Glu  Ala  Glu  Gly
               420                 425                      430

Ala  Gly  Val  Val  Glu  Leu  Ser  Gly  Ile  His  Ile  Ala  Glu  Leu  Arg  Leu
          435                 440                      445

Gly  Asn  Gly  Gly  Ser  Ile  Phe  Lys  Leu  Ala  Asp  Gly  Thr  Val  Ile  Asn
     450                 455                      460

Gly  Pro  Val  Asn  Gln  Asn  Ala  Leu  Met  Asn  Asn  Asn  Ala  Leu  Ala  Ala
465                      470                      475                      480

Gly  Ser  Ile  Gln  Leu  Asp  Gly  Ser  Ala  Ile  Ile  Thr  Gly  Asp  Ile  Gly
               485                      490                      495

Asn  Gly  Gly  Val  Asn  Ala  Ala  Leu  Gln  His  Ile  Thr  Leu  Ala  Asn  Asp
               500                 505                      510

Ala  Ser  Lys  Ile  Leu  Ala  Leu  Asp  Gly  Ala  Asn  Ile  Ile  Gly  Ala  Asn
          515                 520                      525

Val  Gly  Gly  Ala  Ile  His  Phe  Gln  Ala  Asn  Gly  Gly  Thr  Ile  Lys  Leu
     530                 535                      540

Thr  Asn  Thr  Gln  Asn  Asn  Ile  Val  Val  Asn  Phe  Asp  Leu  Asp  Ile  Thr
545                      550                      555                      560

Thr  Asp  Lys  Thr  Gly  Val  Val  Asp  Ala  Ser  Ser  Leu  Thr  Asn  Asn  Gln
               565                      570                      575

Thr  Leu  Thr  Ile  Asn  Gly  Ser  Ile  Gly  Thr  Val  Val  Ala  Asn  Thr  Lys
               580                      585                      590

Thr  Leu  Ala  Gln  Leu  Asn  Ile  Gly  Ser  Ser  Lys  Thr  Ile  Leu  Asn  Ala
          595                      600                      605

Gly  Asp  Val  Ala  Ile  Asn  Glu  Leu  Val  Ile  Glu  Asn  Asn  Gly  Ser  Val
     610                      615                      620

Gln  Leu  Asn  His  Asn  Thr  Tyr  Leu  Ile  Thr  Lys  Thr  Ile  Asn  Ala  Ala
625                      630                      635                      640

Asn  Gln  Gly  Gln  Ile  Ile  Val  Ala  Ala  Asp  Pro  Leu  Asn  Thr  Asn  Thr
               645                      650                      655

Thr  Leu  Ala  Asp  Gly  Thr  Asn  Leu  Gly  Ser  Ala  Glu  Asn  Pro  Leu  Ser
               660                      665                      670

Thr  Ile  His  Phe  Ala  Thr  Lys  Ala  Ala  Asn  Ala  Asp  Ser  Ile  Leu  Asn
          675                      680                      685

Val  Gly  Lys  Gly  Val  Asn  Leu  Tyr  Ala  Asn  Asn  Ile  Thr  Thr  Asn  Asp
```

```
                690                         695                           700
Ala  Asn  Val  Gly  Ser  Leu  His  Phe  Arg  Ser  Gly  Gly  Thr  Ser  Ile  Val
705                      710                      715                       720

Ser  Gly  Thr  Val  Gly  Gly  Gln  Gln  Gly  His  Lys  Leu  Asn  Asn  Leu  Ile
                    725                      730                      735

Leu  Asp  Asn  Gly  Thr  Thr  Val  Lys  Phe  Leu  Gly  Asp  Thr  Thr  Phe  Asn
               740                      745                      750

Gly  Gly  Thr  Lys  Ile  Glu  Gly  Lys  Ser  Ile  Leu  Gln  Ile  Ser  Asn  Asn
          755                      760                      765

Tyr  Thr  Thr  Asp  His  Val  Glu  Ser  Ala  Asp  Asn  Thr  Gly  Thr  Leu  Glu
     770                      775                      780

Phe  Val  Asn  Thr  Asp  Pro  Ile  Thr  Val  Thr  Leu  Asn  Lys  Gln  Gly  Ala
785                      790                      795                       800

Tyr  Phe  Gly  Val  Leu  Lys  Gln  Val  Ile  Ile  Ser  Gly  Pro  Gly  Asn  Ile
                    805                      810                      815

Val  Phe  Asn  Glu  Ile  Gly  Asn  Val  Gly  Ile  Val  His  Gly  Ile  Ala  Ala
               820                      825                      830

Asn  Ser  Ile  Ser  Phe  Glu  Asn  Ala  Ser  Leu  Gly  Thr  Ser  Leu  Phe  Leu
          835                      840                      845

Pro  Ser  Gly  Thr  Pro  Leu  Asp  Val  Leu  Thr  Ile  Lys  Ser  Thr  Val  Gly
     850                      855                      860

Asn  Gly  Thr  Val  Asp  Asn  Phe  Asn  Ala  Pro  Ile  Val  Val  Ser  Gly
865                      870                      875                       880

Ile  Asp  Ser  Met  Ile  Asn  Asn  Gly  Gln  Ile  Ile  Gly  Asp  Lys  Lys  Asn
                    885                      890                      895

Ile  Ile  Ala  Leu  Ser  Leu  Gly  Ser  Asp  Asn  Ser  Ile  Thr  Val  Asn  Ala
               900                      905                      910

Asn  Thr  Leu  Tyr  Ser  Gly  Ile  Arg  Thr  Thr  Lys  Asn  Asn  Gln  Gly  Thr
          915                      920                      925

Val  Thr  Leu  Ser  Gly  Gly  Met  Pro  Asn  Asn  Pro  Gly  Thr  Ile  Tyr  Gly
     930                      935                      940

Leu  Gly  Leu  Glu  Asn  Gly  Ser  Pro  Lys  Leu  Lys  Gln  Val  Thr  Phe  Thr
945                      950                      955                       960

Thr  Asp  Tyr  Asn  Asn  Leu  Gly  Ser  Ile  Ile  Ala  Asn  Asn  Val  Thr  Ile
                    965                      970                      975

Asn  Asp  Asp  Val  Thr  Leu  Thr  Thr  Gly  Gly  Ile  Ala  Gly  Thr  Asp  Phe
               980                      985                      990

Asp  Ala  Lys  Ile  Thr  Leu  Gly  Ser  Val  Asn  Gly  Asn  Ala  Asn  Val  Arg
          995                      1000                     1005

Phe  Val  Asp  Ser  Thr  Phe  Ser  Asp  Pro  Arg  Ser  Met  Ile  Val  Ala  Thr
     1010                     1015                     1020

Gln  Ala  Asn  Lys  Gly  Thr  Val  Thr  Tyr  Leu  Gly  Asn  Ala  Leu  Val  Ser
1025                     1030                     1035                      1040

Asn  Ile  Gly  Ser  Leu  Asp  Thr  Pro  Val  Ala  Ser  Val  Arg  Phe  Thr  Gly
                    1045                     1050                     1055

Asn  Asp  Ser  Gly  Ala  Gly  Leu  Gln  Gly  Asn  Ile  Tyr  Ser  Gln  Asn  Ile
               1060                     1065                     1070

Asp  Phe  Gly  Thr  Tyr  Asn  Leu  Thr  Ile  Leu  Asn  Ser  Asn  Val  Ile  Leu
          1075                     1080                     1085

Gly  Gly  Gly  Thr  Thr  Ala  Ile  Asn  Gly  Glu  Ile  Asp  Leu  Leu  Thr  Asn
     1090                     1095                     1100

Asn  Leu  Ile  Phe  Ala  Asn  Gly  Thr  Ser  Thr  Trp  Gly  Asp  Asn  Thr  Ser
1105                     1110                     1115                      1120
```

```
Ile Ser Thr Thr Leu Asn Val Ser Ser Gly Asn Ile Gly Gln Val Val
            1125                1130                1135
Ile Ala Glu Asp Ala Gln Val Asn Ala Thr Thr Thr Gly Thr Thr Thr
            1140                1145                1150
Ile Lys Ile Gln Asp Asn Ala Asn Ala Asn Phe Ser Gly Thr Gln Ala
            1155                1160                1165
Tyr Thr Leu Ile Gln Gly Gly Ala Arg Phe Asn Gly Thr Leu Gly Ala
            1170                1175                1180
Pro Asn Phe Ala Val Thr Gly Ser Asn Ile Phe Val Lys Tyr Glu Leu
1185                1190                1195                1200
Ile Arg Asp Ser Asn Gln Asp Tyr Val Leu Thr Arg Thr Asn Asp Val
            1205                1210                1215
Leu Asn Val Val Thr Thr Ala Val Gly Asn Ser Ala Ile Ala Asn Ala
            1220                1225                1230
Pro Gly Val Ser Gln Asn Ile Ser Arg Cys Leu Glu Ser Thr Asn Thr
            1235                1240                1245
Ala Ala Tyr Asn Asn Met Leu Leu Ala Lys Asp Pro Ser Asp Val Ala
            1250                1255                1260
Thr Phe Val Gly Ala Ile Ala Thr Asp Thr Ser Ala Ala Val Thr Thr
1265                1270                1275                1280
Val Asn Leu Asn Asp Thr Gln Lys Thr Gln Asp Leu Leu Ser Asn Arg
            1285                1290                1295
Leu Gly Thr Leu Arg Tyr Leu Ser Asn Ala Glu Thr Ser Asp Val Ala
            1300                1305                1310
Gly Ser Ala Thr Gly Ala Val Ser Ser Gly Asp Glu Ala Glu Val Ser
            1315                1320                1325
Tyr Gly Val Trp Ala Lys Pro Phe Tyr Asn Ile Ala Glu Gln Asp Lys
            1330                1335                1340
Lys Gly Gly Ile Ala Gly Tyr Lys Ala Lys Thr Thr Gly Val Val Val
1345                1350                1355                1360
Gly Leu Asp Thr Leu Ala Ser Asp Asn Leu Met Ile Gly Ala Ala Ile
            1365                1370                1375
Gly Ile Thr Lys Thr Asp Ile Lys His Gln Asp Tyr Lys Lys Gly Asp
            1380                1385                1390
Lys Thr Asp Ile Asn Gly Leu Ser Phe Ser Leu Tyr Gly Ser Gln Gln
            1395                1400                1405
Leu Val Lys Asn Phe Phe Ala Gln Gly Asn Ser Ile Phe Thr Leu Asn
            1410                1415                1420
Lys Val Lys Ser Lys Ser Gln Arg Tyr Phe Phe Glu Ser Asn Gly Lys
1425                1430                1435                1440
Met Ser Lys Gln Ile Ala Ala Gly Asn Tyr Asp Asn Met Thr Phe Gly
            1445                1450                1455
Gly Asn Leu Ile Phe Gly Tyr Asp Tyr Asn Ala Met Pro Asn Val Leu
            1460                1465                1470
Val Thr Pro Met Ala Gly Leu Ser Tyr Leu Lys Ser Ser Asn Glu Asn
            1475                1480                1485
Tyr Lys Glu Thr Gly Thr Thr Val Ala Asn Lys Arg Ile Asn Ser Lys
            1490                1495                1500
Phe Ser Asp Arg Val Asp Leu Ile Val Gly Ala Lys Val Ala Gly Ser
1505                1510                1515                1520
Thr Val Asn Ile Thr Asp Ile Val Ile Tyr Pro Glu Ile His Ser Phe
            1525                1530                1535
Val Val His Lys Val Asn Gly Lys Leu Ser Asn Ser Gln Ser Met Leu
            1540                1545                1550
```

| | | | | | | | | | | | | | |
|---|---|---|---|---|---|---|---|---|---|---|---|---|---|
| Asp | Gly | Gln 1555 | Thr | Ala | Pro | Phe | Ile 1560 | Ser | Gln | Pro | Asp | Arg 1565 | Thr Ala Lys |
| Thr | Ser 1570 | Tyr | Asn | Ile | Gly | Leu 1575 | Ser | Ala | Asn | Ile | Lys 1580 | Ser | Asp Ala Lys |
| Met 1585 | Glu | Tyr | Gly | Ile | Gly 1590 | Tyr | Asp | Phe | Asn | Ser 1595 | Ala | Ser | Lys Tyr Thr 1600 |
| Ala | His | Gln | Gly | Thr 1605 | Leu | Lys | Val | Arg | Val 1610 | Asn | Phe | | |

GENE AND PROTEIN APPLICABLE TO THE PREPARATION OF VACCINES FOR *RICKETTSIA PROWAZEKII* AND *RICKETTSIA TYPHI* AND THE DETECTION OF BOTH

RELATED APPLICATIONS

This application is a continuation-in-part of U.S. patent application Ser. No. 07/742,128, filed 9 Aug. 1991, now abandoned.

BACKGROUND OF THE INVENTION

1. Field of the Invention

This invention relates to a gene and protein which can be used for vaccination against and/or for the detection and identification of *R. typhi* and *R. prowazekii*. More particularly, the invention relates to the DNA sequence of the gene encoding the protective S-layer protein antigen of *Rickettsia prowazekii* and the products of this gene.

2. Description of the Prior Art

*R. prowazekii* is the etiological agent of epidemic typhus and is well established in its primary host, man. The human body louse is the primary vector. The occurrence of typhus parallels the history of war and famine. Thirty million cases of typhus occurred in Eastern Europe and Russia during World War I and during the years immediately following. In addition, during World War II, typhus was widespread in concentration camps in Eastern Europe and in North Africa. There are still foci of epidemic typhus infection throughout the world including the Andes region of South America, Ethiopia, Mexico, Eastern Europe, China, the Soviet Union, the Middle East, and parts of Southeast Asia. In addition, the flying squirrel and its louse and flea ectoparasites has been identified as a carrier of *R. prowazekii* in Southeast portions of the United States.

The etiologic agent of epidemic typhus, *Rickettsia prowazekii*, is an obligate intracellular bacterium. The disease is usually transmitted from person to person by the human body louse (*Pediculus humanus corporis*). The actual disease source is louse feces. This can be introduced to a host by scarification of the louse feces into a bite wound, aerosol inhalation or open wound contact with louse feces and other similar or related pathways. Following local growth at the site of entry, the organism spreads and causes a vasculitis by infecting the endothelial cells of capillaries, small arteries, and veins. Mortality has been reported to be as high as 60%.

Vaccination against rickettsial disease has a long history, Topping et al., *Ann. Rev. Microbiol.*, 1, pp.333–350 (1947). Weigl and Castaneda prepared vaccines against epidemic typhus in the 1930s from infected lice and infected rodent lungs. Mass production of vaccines followed. These types of vaccines are not used today because they no longer meet modern standards for bacterial vaccines. If safety and efficacy standards can be satisfied, vaccination would be a cost effective and desirable means of protecting defined populations.

Abundant evidence has been obtained that the crystalline surface layer protein antigens (SPAs) of the typhus group rickettsiae, *R. prowazekii* and *Rickettsia typhi*, and of the spotted fever group rickettsiae can serve as effective immunogens in animal models (Bourgeois et al, *Rickettsiae and rickettsial diseases*, pp.71–80, Academic Press, Inc., New York (1981); Ching et al, *Ann. N.Y. Acad. Sci.*, 590, pp.334–351 (1990); Dasch, *J. Clin. Microbiol.*, 14, pp.333–341 (1981); Dasch et al, *Rickettsiae and rickettsial diseases*, pp.61–70, Academic Press, Inc., New York (1981); Dasch et al, *Rickettsiae and rickettsial diseases*, pp.54–61, Publishing House of the Slovak Academy of Sciences, Bratislava (1985); Dasch et al, *Microbiology*, pp.251–256, American Society for Microbiology, Washington, D.C. (1984); Dasch et al, *Infect. Immun.*, 31, pp.276–288 (1981); McDonald et al, *Science*, 235, pp.83–85 (1987); McDonald et al, *J. Infect. Dis.*, 158, pp.228–231 (1988); Vishwanath et al, *Infect. Immun.*, 58, pp.646–653 (1990)). In addition, the SPAs can elicit both antibody and cell-mediated immune responses in both experimental animal models and in man (Carl et al, *J. Immunol.*, 136, pp.2654–2658 (1986); Carl et al, *J. Immunol.*, 139, pp.4203–4207 (1987); Carl et al, *J. Autoimmunity*, 2, pp.81–91 (1989); Carl et al, *Infect. Immun.*, 57, pp.1276–1280 (1989); Misiti et al, *J. Immunol.*, 134, pp.2689–2694 (1985)).

The major problem with SPA vaccines to be surmounted is the large scale production of the antigen. Although nontoxic and efficacious lots of antigen can be obtained directly from typhus rickettsiae (Bourgeois et al, *Rickettsiae and rickettsial diseases*, pp.71–80, (1981); Dasch, *J. Clin. Microbiol.*, 14, pp.333–341 (1981); Dasch et al, *Rickettsiae and rickettsial diseases*, pp.61–70 (1981)), the cost and hazard of manufacturing vaccine directly from the rickettsiae is formidable. Vaccine development would therefore be greatly facilitated by expressing the SPA in vectors capable of expressing large quantities of antigen.

In addition, the prognosis in rickettsial infections depend largely on the initiation of appropriate antibiotic therapy early in the course of the illness. Therefore, methods and materials which would lead to the more rapid diagnosis of rickettsial infections would presumably result in improved prognosis.

SUMMARY OF THE INVENTION

Accordingly, an object of this invention is to provide large quantities of S-layer protein.

Another object of this invention is to provide large quantities of S-layer protein in a form in which it can be used for vaccination against endemic rickettsial infection.

An additional object of this invention are tests designed to diagnose epidemic and endemic typhus.

Yet another object of this invention is to provide sufficient quantities of materials having DNA sequences of the gene which encodes the S-layer protein of *R. prowazekii*.

A further object of this invention is to provide the 5' and 3' non-coding regions of the S-layer protein from which primers may be generated to be used in the polymerase chain reaction for the rapid diagnosis of both epidemic and endemic typhus.

These and additional objects of the invention are accomplished by providing all or part of the DNA sequence of the gene which encodes the S-layer protein of *R. prowazekii* as illustrated in Sequence Listing I and an identical truncated portion of this gene in *R. typhi* as well as the 5' and 3' noncoding regions. The invention is also accomplished by the deduced amino acid sequence of the S-layer protein of *R. prowazekii* derived from the DNA sequence of the encoding gene homologs, and variants together with a suitable vector. Further, the invention includes the protein products of all or parts of this gene.

BRIEF DESCRIPTION OF THE DRAWINGS

A more complete appreciation of the invention will be readily obtained by reference to the following Description of the Preferred Embodiments and the accompanying drawings in which like numerals in different figures represent the same structures or elements. The representations in each of the figures is diagrammatic and no attempt is made to indicate actual scales or precise ratios. Proportional relationships are shown as approximations.

FIG. 3A depicts the Hydropathy profile.

FIG. 3B depicts the alpha helical structure.

FIG. 3C depicts beta sheet structure.

SEQUENCE LISTING

Figure 1:
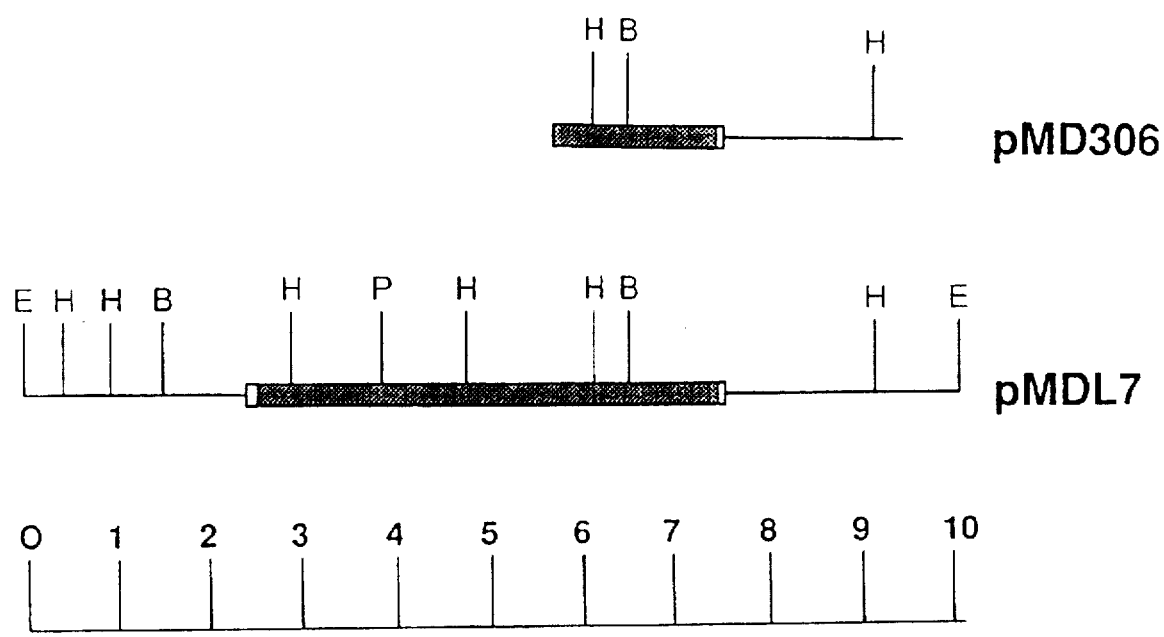
FIG. 1 shows restriction maps of the rickettsial inserts of recombinant pUC plasmids.

Seq. ID #1—DNA sequence of the gene which encodes the S-layer protein of R. prowazekii as well as 5' and 3' non-coding regions.

Seq. ID #2—Deduced amino acid sequence of the S-layer protein of R. prowazekii.

DEPOSIT INFORMATION

The Escherichia coli DH5α carrying plasmid pMDL7, MD 192 has been deposited on 18 Oct. 1993 and has been accepted at the American Type Culture Collection (ATCC), 12301 Parklawn Drive, Rockville, Md. 20852, USA under the terms of the Budapest Treaty for a period of thirty (30) years. The ATCC Designation number is 69473. Under the terms of the deposit, access to the culture will be available during pendency of the patent application to one determined by the Commissioner of Patents and Trademarks to be entitled thereto under 37 C.F.R. 1.14 and 35 U.S.C. § 122, and all restrictions on the availability to the public of the culture so deposited will be irrevocably removed upon granting of the patent.

DESCRIPTION OF THE PREFERRED EMBODIMENTS

Gene libraries from R. prowazekii Breinl and R. typhi Wilmington were constructed in the expression vector, lambda gt11. In addition, recombinant lambda gtWES bacteriophages containing either a 10.1 kb R. prowazekii Breinl-derived DNA fragment or an 8.7 kb R. typhi Wilmington-derived DNA fragment were also constructed. Recombinant phages expressing fragments or the entire rickettsial crystalline surface layer protein antigen (SPA) of either R. prowazekii or R. typhi were identified on plaque lifts using a mixture of monoclonal antibodies directed against different linear epitopes present on the SPA.

From the R. prowazekii-derived library, three purified phage were used to stably lysogenize E. coli strain Y1089 (r–). Two of the lysogens, MD103 and MD104, contained fusion proteins with apparent molecular weights of 135 and 160 kDa, respectively, since they contained bands which reacted with rabbit antibody against beta-galactosidase and the anti-SPA monoclonal antibody pool. The fusion proteins therefore contained approximately 25 and 50 kDa of SPA antigen. The remaining lysogen, MD101 did not react with the anti-SPA monoclonal antibody pool on Western blots although it was immunoreactive on plaque lifts. However, since the beta-galactosidase reactive bands of MD101 fractionated to the cell envelope like the MD103 and MD104 products, and all three extracts contained a 98 kDa truncated form of beta-galactosidase which did not react with anti-SPA antibodies, it appears that MD101 also expresses an SPA fusion protein. However, it seems to be weakly immunoreactive and very short since the fusion protein had a molecular weight quite comparable to control beta-galactosidase.

The R. prowazekii-derived lambda gtWES clone (lambda gtWES/PB3.2) was found to produce SPA products whose size distribution was greater than that of the SPA obtained from the rickettsiae. Recombinant plasmids pMD306 was created by subcloning the 3.7 kb insert derived from MD104 into pUC 8. Similarly, pMDL7 was created by subcloning the 10.1 kb insert derived from lambda gtWES/PB3.2 into pUC 8. Therefore, several strains of E. coli have been obtained which produce part or all of the S-layer protein antigen (SPA) of Rickettsia prowazekii, the major component of the rickettsial outer surface (Ching, W-M. et al; Ann. N. Y. Acad. Sci.; 590 p.334–351; 1990. Dasch, G. A.; J. Clin. Microbiol.; 14 p.333–341; 1981. Dasch, G. A. et al; Infect. Immun.; 31 p.276–288; 1981). The SPA epitopes were expressed as different sized fragments fused to the carboxy-terminal region of beta-galactosidase by lysogenized strains, MD101, MD103 and MD104, or as the entire protein by lambda gtWES/PB3.2. Initial evidence that the cloned gene was SPA included immunological reactivity of the products with several monoclonal antibodies with specificity for typhus SPA, and comparison of the size of the expressed protein with the rickettsia-derived SPA. Since the SPA is expressed in lambda gtWES/PB3.2 constitutively, it is clear that the full rickettsial promoter and ribosome binding sites are present. This is also clear after examining the complete nucleotide sequence for the R. prowazekii-derived SPA gene (spaP).

The complete nucleotide sequences of plasmids pMD306 and pMDL7 were determined for both strands of DNA. The entire sequence of pMD306 was contained within pMDL7. Sequencing of both strands of pMDL7 revealed a gene (spaP) with an open reading frame of 4,836 nucleotides between the ATG triplet at position 394 to 396 and the TAA stop codon at position 5230 to 5232. Presumptive ribosome-binding site and –10 and –35 regions were identified. A large inverted repeat forming a stem loop structure consisting of a 14 bp stem and an 11 bp loop is present downstream of the translational stop codons (nucleotides 5271–5309) and might function as a transcriptional termination signal. N-terminal amino acid sequences of eight CNBr fragments of purified R. prowazekii SPA were found within the open reading frame. The DNA sequence predicts the existence of an additional seven CNBr fragments at the carboxy end of the SPA with molecular weights of 0.87 to 8.14 kD. However, despite the fact that all other major CNBr fragments throughout the rest of the molecule were identified, no fragments corresponding to these seven predicted carboxy terminal fragments could be found. A 5.5 kD CNBr fragment beginning at amino acid 1255 (corresponding to nucleic acids 4216–4218) was closest to the putative SPA carboxy terminus.

The recombinant SPA products exhibited three unexpected properties. First, unlike the natural SPA which can be readily extracted from the rickettsia in aqueous media (Dasch, G. A.; 1981), the fused recombinant products and the lambda gtWES/PB3.2 SPA product were strongly associated with the envelope fraction. A computer generated hydropathy plot of the deduced amino acid sequence revealed several regions of hydrophobicity with little or no hydrophilic regions (Carl, M. et al; *Proc. Nat. Acad. Sci.;* 87, pp. 8237–8241, 1990). This might account for the observed localization of the fusion peptides although even the truncated beta-galactosidase molecule which is apparently derived by proteolytic processing of the recombinant proteins also partitioned into the envelope fraction and might be the cause of this unexpected partitioning. Neither explanation seems satisfactory for the full length recombinant protein. It is striking that all the recombinant SPA fragments derived from the full length recombinant protein also partitioned into the envelope fraction (data not shown). Most likely the SPA does not fold properly in its *E. coli* environment. Conformationally-sensitive anti-SPA monoclonal antibodies did not bind to either lambda gtWES/PB3.2 plaque lifts or envelope fractions containing recombinant SPA, even when the latter were examined by Western blotting under conditions which permit their binding to rickettsia-derived SPA (data not shown). Denatured or fragmented rickettsia-derived typhus SPA also has poor solubility properties (W-M. Ching and G. A. Dasch, unpublished properties).

A second surprising aspect of the recombinant SPA product was that it appeared larger than the majority fraction of rickettsial SPA detected by Coomassie staining or by Western blotting. This is consistent with the 169 kD protein which is encoded by the spaP gene (Carl, M.; 1990). Although *R. prowazekii*-derived SPA has an estimated molecular weight of 120 kD, the spaP gene encodes a protein with a molecular weight of 169.87 kD. Although widely disparate molecular weights for the SPA have been obtained by different methods and it migrates anomalously by PAGE (Ching, W-M. et al; *Ann. N. Y. Acad. Sci.;* 590 p.334–351; 1990. Smith, D. K. et al; *J. Bact.;* 137 p.963–971; 1979. Ching, W-M. et al; *J. Cell. Biochem.;* 13A p.51; 1989), this discrepancy is rather large. However, seven CNBr fragments predicted at the carboxy end of the molecule from the deduced amino acid sequence were not present in the rickettsia-derived SPA.

It is striking that the carboxy end of the SPA for *R. prowazekii* contains both a hydrophobic region with alpha-helical configuration consisting of 24 amino acids (amino acids 1356–1379 corresponding to nucleic acids 4519–4590), which could span the bacterial cell membrane, and an adjacent 16 hydrophilic amino acids in a beta turn region (amino acids 1382–1396 corresponding to nucleic acids 4597–4641) could serve respectively as a hydrophobic anchor and translocation stop. This is consistent with what is presently known about hydrophobic anchor sequences which have been identified in transmembrane proteins (Eisenberg, D. A., *Ann. Rev. Biochem.,* 53 p.595–623 (1984). Davis, G. D. et al, *J. Mol. Biol.,* 181 p.111–121, (1985). Cleavage of the SPA protein near this anchor region would then result in a soluble surface protein with approximately the same molecular weight (130 kD) and almost the identical amino acid composition as determined for *R. prowazekii*-derived SPA (Ching et al, 1990).

Although the calculated pI of 5.4 for the protein which results from this hypothesized cleavage would differ from the pI of 4.1 already determined for the SPA (Oaks, E. V. et al; in Rickettsiae and Rickettsial Diseases, eds. Burgdorfer, W. & Anacker, R. L.; Academic Press, New York, N.Y.; p.461–472; 1981), there are various modifications of the protein which might account for this difference. Multiple methylation of lysine residue has been detected on the rickettsial SPA (Ching, et al., Techniques in Protein Chemistry, Vol IV, pp 307–314, Academia Press, 1993). Other post translational modifications such as phosphorylation, deamidation, and methylation of other amino acid residues are also possible, but no glycosylation has been found. In the rickettsiae some SPA antigen which reacts with monoclonal antibodies is always detected at significantly higher molecular weights than the major SPA species (Ching, W-M. et al; *Ann. N. Y. Acad. Sci.;* 590 p.334–351; 1990). This high molecular weight SPA most likely represents unprocessed SPA. In spite of being grown in the protease deficient host, Y1090(r−), much of the recombinant SPA protein was present as fragments smaller than the major form of the native protein. Although such fragmentation is also observed with the rickettsia-derived SPA (Ching, W-M.; 1990), these fragments comprise a much smaller percentage of the total antigen present than they do in the recombinant strain. This SPA degradation could be a response of the host cell to a foreign protein product.

A similar pattern of fragments has also been seen for the cloned large SPA of *R. rickettsia* (McDonald, G. A. et al; *Science;* 235 p.83–85; 1987). Although fragments of the rickettsial SPA might arise from proteases acting on the S-layer while the rickettsiae grow in the cytoplasm of their host cells, hypotonic-shock extracted SPA (Dasch, G. A.; 1981) is relatively insensitive to a variety of proteases unless it is heated to non-physiological conditions or treated with detergents or chaotropic agents (Dasch, unpublished observations).

The entire SPA or fragments of the SPA illustrated in FIGS. 2A and B (Seq. ID #2) serves as the basis for a subunit vaccine against typhus and possibly spotted fever rickettsia. The purified protein in the presence or absence of adjuvant is injected intramuscularly or intradermally. The plasmid is combined with a vector in the manor known in the art. The plasmid and vector can be formed from the entire material or from homologs, fragments and variants. Primers of at least one selected from the 5' end and one from the 3' end can be used in PCR and other known tests to rapidly identify the rickettsial disease.

Having described the invention, the following examples are given to illustrate specific applications of the invention including the best mode now known to perform the invention. These specific examples are not intended to limit the scope of the invention described in this application.

EXAMPLE 1

Preparation and Immunoreactivity of Lambda gt11 Library of *Rickettsia prowazekii*

The origin, passage history, and biological properties of *Rickettsia prowazekii* strain Breinl and *Rickettsia typhi* strain Wilmington have been described in detail elsewhere (Woodman, D. R. et al; *Infect. Immun.;* 16 p.853–860; 1977). The rickettsiae were grown in 6 day old embryonated chicken eggs and purified by Renografin density gradient centrifugation (Dasch, G. A.; 1981. Dasch, G. A. et al; *Infect. Immun.;* 15 p.280–286; 1977). DNA was prepared from 100 mg protein of purified rickettsiae as previously described (Maniatis, T. et al; Cold Spring Harbor Laboratory, Cold Spring Harbor, N.Y.; 1982). Purified rickettsial DNA (90 ug) was partially digested with a mixture of Alu I (0.01 U/ug), Hae III (0.04 U/ug), and Rsa I (0.01 U/ug), size fractionated in the 2–9 kb range on a sucrose gradient (Maniatis, T.; 1982), and ligated to Eco RI linkers with T4 DNA ligase after treatment with Eco RI methylase. Linkered DNA was then ligated into Eco RI digested, dephosphorylated lambda gt11 (Promega Biotech, Madison, Wis.). Portions of the ligation reaction were packaged into phage with PackaGene (Promega Biotech, Madison, Wis.) using protocols supplied by Promega. Recombinant lambda gt11 phage were grown and purified as previously described (Maniatis, T.; Lambdasorb, Promega Biotech, Madison, Wis.; 1982).

Phage were plated at approximately $10^3$ per 150 mm dish on maltose-induced *E. coli* Y1090(r−) grown on TB plates (1% tryptone, 0.5% NaCl) containing X-Gal (5-bromo-4-chloro-3-indolyl-beta-D-galactoside, 0.02%) (Davis, L. G. et al; Basic methods in molecular biology; Elsevier, N.Y.; 1986). Plaque lifts were screened using a mixture of 4 monoclonal antibodies (Raoult, D. et al; *J. Immunol. Meth.*; 125 p.57–65; 1989) (PT47-1C5.1, P53-2D7.1, P53-2D10.1, P53-5E12.1), affinity purified rabbit anti-mouse IgG, and $^{125}$I-labeled Staphylococcus protein A (New England Nuclear). Immunoreactive plaques were replated at 100–200 plaques per plate, rescreened as above, and replated until purified. Stable lysogens were selected in the hfl strain, Y1089(r−), and stored frozen at −70° C.

The packaged DNA produced $3 \times 10^5$ phage of which 92% contained recombinant inserts of 1–6 kb size. Assuming a genome size of 1.5 Mb (Myers, W. F. et al; *Int. J. Syst. Bacteriol;* 30 p.143–150; 1980) and an average insert size of 3 kb, a typical packaging of this size should contain 550 copies of the genome. One thousand recombinant phage plaques per plate were screened with a pool of monoclonal antibodies directed against a variety of linear epitopes present on the purified SPA of *Rickettsia prowazekii*. Eleven immuno-reactive plaques were obtained from 20,000 plaques containing an estimated 36 genomic copies. Nine of these phage were plaque purified without loss of immunoreactivity. The purified phage were used to stably lysogenize *E. coli* strain Y1089(r−). The recombinant products expressed by three lysogens following heat and isopropyl-beta-thiogalactopyranoside (IPTG) induction were characterized by SDS-PAGE and Western blotting. Two lysogens, MD103 and MD104, contained fusion proteins with apparent molecular weights of 135 and 160 kDa, respectively, since they contained bands which reacted with rabbit antibody against beta-galactosidase and the anti-SPA monoclonal antibody pool. The fusion proteins therefore contained approximately 25 and 50 kDa of SPA antigen. The SPA fusion proteins also localized in the cell envelope fraction but not in the cytoplasm or concentrated broth, unlike control extracts which contained soluble beta-galactosidase in both the medium and cytoplasmic extracts.

The remaining strain MD101 did not react with the anti-SPA monoclonal antibody pool on Western blots although it was immunoreactive on plaque lifts. However, since the beta-galactosidase reactive bands of MD101 fractionated to the cell envelope like the MD103 and MD104 products, and all three extracts contained a 98 kDa truncated form of beta-galactosidase which did not react with anti-SPA antibodies, it appears that MD101 also expresses an SPA fusion protein. However, it seems to be weakly immunoreactive and very short since the fusion protein had a molecular weight quite comparable to control beta-galactosidase.

Recombinant phage DNAs were analyzed by restriction digestion and agarose gel electrophoresis (Maniatis; 1982). The Eco RI inserts from recombinant lambda gt11 phage were prepared by Eco RI digestion, ligated into pUC8 (Maniatis; 1982) without purification, and used to transform *E. coli* DH5 (Bethesda Research Laboratories (BRL)). DNA from recombinant plasmids (Maniatis; 1982) were analyzed by agarose gel electrophoresis after restriction digestion. MD104, which expressed the largest fragment of SPA, contained a 3.7 kb DNA insert bounded by the Eco RI linkers that was subcloned into the Eco RI site of pUC 8. The resultant plasmid, pMD306 was partially mapped with several restriction enzymes (FIG. 1); FIG. 1 shows restriction maps of the rickettsial inserts of four recombinant pUC plasmids. The inserts from pMD306 and pMDL7 are derived from *R. prowazekii.* Boxes represent sequenced regions; a shaded area represents a continuous open reading frame. Restriction endonucleases used include Bgl II (B), Eco RI (E), Hind II (H), Pst I (P). The scale is in kilobases.

EXAMPLE 2

Southern Blotting

In order to identify a genomic fragment which might contain the entire gene encoding the *R. prowazekii* and the *R. typhi* SPA, pMD306 was labeled by nick translation and used as a probe of *R. prowazekii* and *R. typhi* genomic DNA digested with Eco RI, Hind III, Eco RV, Aha III, Hinf I, and Rsa I. Recombinant plasmid DNA was labeled with $^{35}$S-dATP by nick translation using a commercial kit (BRL). Alternatively, probes were generated using polymerase chain reaction-derived products labeled with digoxigenin (Carl, M. et al; *J. Inf. Dis.;* 161 p.791–794; 1990) and detection was accomplished using stringent conditions as recommended by the manufacturer (Boehringer-Mannheim). Rickettsial or recombinant phage DNAs were digested with the appropriate restriction enzymes, electrophoresed in 0.7% agarose gels, and transferred to nitrocellulose (Schleicher & Schuell). Hybridizations were carried out largely as described by Southern (Southern, E. M.; *J. Mol. Biol.;* 98 p.503–517; 1975). For *R. prowazekii,* hybridization was observed to a single, large, Eco RI fragment of about 10 Kb and less distinctly to a slightly larger Eco RV fragment. The other genomic fragments detected were smaller than the estimated 3.6 Kb needed to encode the entire SPA protein. Since pMD306 did not contain an internal Eco RI site, it was expected that a clone containing pMD306 on a 10 Kb Eco RI fragment would encode the entire SPA gene.

EXAMPLE 3

Construction and Screening of Eco R1 Lambda gtWES Library and Subcloning

A total Eco RI digested library of *R. prowazekii* DNA was constructed in lambda gtWES. The ligated DNA was packaged in vitro, and the recombinant phage were plated on the host strain, ED8654. Approximately $5\times10^4$ phage (nearly 100% containing inserts) were obtained from an experiment where 0.1 μg of phage arms were packaged. From screens of 6000 recombinant phage, 10 small *R. prowazekii*-derived plaques were obtained which reacted with the anti-SPA monoclonal antibodies. Since these phage proved difficult to plaque purify, only a single immunoreactive purified phage, lambda gtWES/PB3.2 was obtained. To confirm that the recombinant phage contained the desired 10 Kb Eco R1 fragment encoding the SPA gene, genomic *R. prowazekii* DNA and recombinant phage DNA were digested with restriction enzymes and Southern blotting was performed with radiolabeled pMD306 DNA as probe. The expected 10 Kb Eco RI fragment, the internal 2.9 Kb Hind III and 2.7 Kb Bgl II fragments present in pMD306 (FIG. 1) and additional 1.3 Kb Hind III and 4.8 Kb Bgl II fragments were all identical in both the recombinant and genomic DNAs, thus indicating the identity of the cloned Eco RI fragment with the desired genomic fragment.

Recombinant plasmid pMDL7 was created by subcloning the 10.1 kb insert (originally derived from *R. prowazekii*

Breinl), from the recombinant lambda gtWES bacteriophages. The restriction maps of this plasmid insert is shown in FIG. 1. This data suggested that the pMD306 insert is identical to a region contained within pMDL7.

EXAMPLE 4

Western Blotting Characterization of Protein Expressed by Lambda gtWES/PB3.2

Phage replication and beta-galactosidase fusion peptides were induced in broth cultures of single colonies of recombinant lysogens as previously described (Maniatis, T.; 1982). To minimize host cell degradation of expressed recombinant protein, fractions of both control lambda gtWES and lambda gtWES/PB3.2 were prepared from lysates of the protease deficient lon strain, Y1090(r−).

Cell pellets were collected by centrifugation for 15 min at 7000× g and suspended in 10 ml of distilled water. The suspensions were broken by passage through a French pressure cell 3 times at 20,000 psi. The extracts were spun for 1 h at 200,000× g, yielding a pelleted envelope fraction and the supernatant cytoplasmic fraction.

The envelope was resuspended in 10 ml $H_2O$ by homogenization. The spent media, resulting from the first low speed centrifugation, was concentrated 10-fold using Centricon-30 units (Amicon). Fractions were stored at −70° C. Fractions were solubilized by boiling for 5 min in 2% SDS and 5% 2-mercaptoethanol, fractionated by SDS-PAGE on 8–16% gradient gels, and transferred to nitrocellulose in 25 mM $NaH_2PO_4$, pH 7.5 as previously described (Raoult, D. et al; *J Clin. Microbiol.*; 27 p.2073–2079; 1989. Towbin, H. et al; *Proc. Nat'l. Acad. Sci.*; 76 p.4350–4354; 1979).

Figure 2:
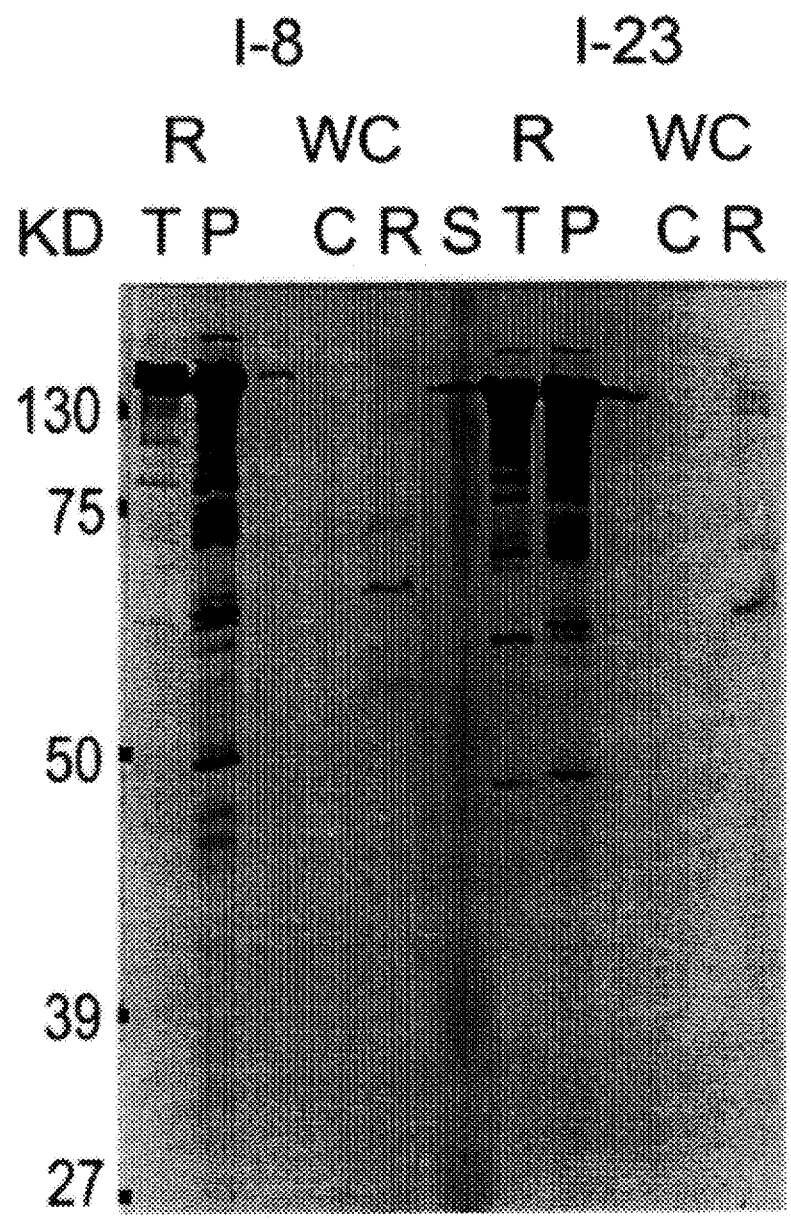
FIG. 2 is a western blot of fractions of control lambda gtWES (C) and recombinant lambda gtWES/PB3.2 phage expressing R. prowazekii SPA gene (R).
Figure 3A:
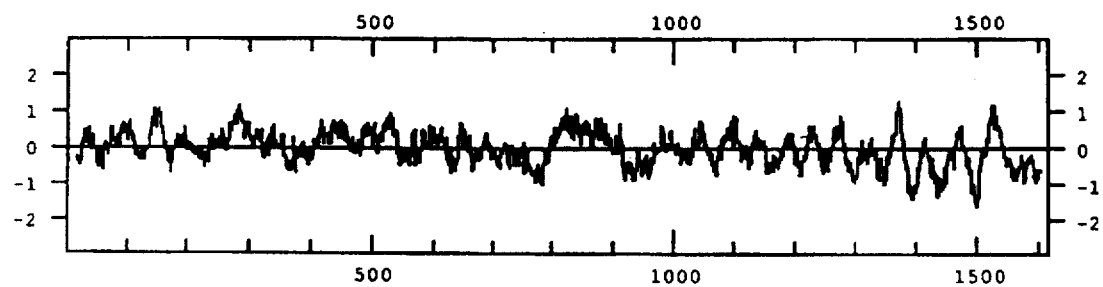
FIG. 3A, FIG. 3B and FIG. 3C are the theoretical structure analysis of the R. prowazekii SPA based on the deduced amino acid sequence.
Figure 3B:
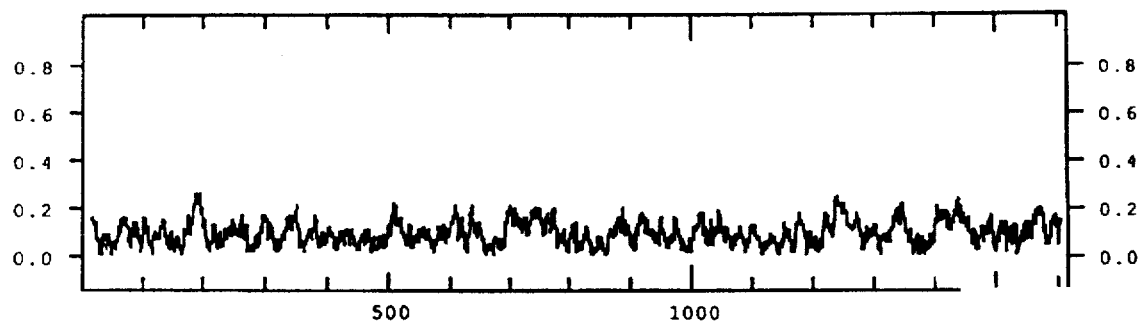
Figure 3C:
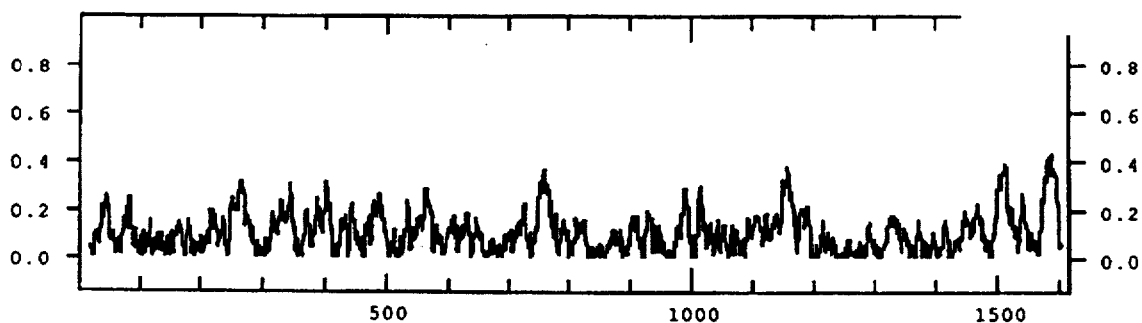

Immunoblot detection was accomplished with $^{125}I$-labelled Staphyloccus protein A or with horseradish peroxidase conjugated goat anti-mouse IgG antisera. Bound enzyme was detected with 0.015% 4-chloro-1-naphthol, 0.015% $H_2O_2$, 16% methanol in TBS. Following fractionation of the extracts, the Western blots were immunodetected with monoclonal antibodies which differed in their reactivity toward linear epitopes of the SPAs of *R. prowazekii* and *R. typhi* (FIGS. 2A and B). FIGS. 2A and B reproduces Western blots of fractions of control lambda gtWES (C) and recombinant lambda gtWES/PB3.2 phage expressing *R. prowazekii* SPA gene (R). Lanes: whole cell lysates of *Rickettsia typhi* (RT) and *R. prowazekii* (RP); WC: whole phage lysates; S: Prestained molecular weight standards (kDa from top: 110, 84, 47, 33, and 24). Two sets of identical samples were separated on the same 8–16% SDS gel and transferred to nitrocellulose. The sheet was then divided using the prestained standards as a guide. Each half sheet was immunodetected by sequential reaction with either PT47-1C5.1 (I-8) or P53-3D1.1 (I-23) anti-SPA monoclonal antibody, horseradish peroxidase conjugated goat anti-mouse IgG, and 4-Cl-1-naphthol/$H_2O_2$ stain. The highest molecular weight form of the recombinant SPA detected is indicated (*). Under these conditions the SPAs of rickettsial whole cell lysates migrate as a major Coomassie blue stainable band at 120 kDa. By Western blotting this major band is accompanied by a single band of greater size and by multiple fragments of lower molecular weight. The lambda gtWES/PB3.2 lysates, but not the control extracts, contained a similar complex array of immunoreactive peptides including material migrating significantly above the major native SPA band at approximately the position of the largest minor band of SPA present in the rickettsial lysates. Like the SPA fragments expressed as fusion proteins with beta-galactosidase, the lambda gtWES/PB3.2 lysates fractionated in the membrane fraction rather than as a soluble protein (data not shown). Unlike the fusion protein in which expression of the fusion protein required IPTG, the lambda gtWES/PB3.2 SPA product was expressed constitutively, presumably using a rickettsial promoter.

EXAMPLE 5

DNA Sequencing

Recombinant plasmids were sequenced directly from plasmid DNA by the chain termination method (Sanger, F. et al; *Proc. Natl. Acad. Sci. USA;* 74 p.5463–5467; 1977) with Sequenase (United States Biochemicals, Inc.) as the polymerase. Sequencing was initiated on both strands using M13 primers (Promega Inc., United States Biochemicals, Inc.). Subsequently, sequencing was continued on both strands using custom synthetic oligonucleotides as primers. The complete nucleotide sequence of plasmid pMD306 was determined for both strands of DNA. The entire sequence for this plasmid was contained within pMDL7. Further sequencing of both strands of pMDL7 revealed an open reading frame of 4,836 nucleotides between the ATG triplet at position 394 to 396 and the TAA stop codon at position 5230 to 5232. Presumptive ribosome-binding site and −10 and −35 regions are underlined. A large inverted repeat forming a stem loop structure consisting of a 14 bp stem and an 11 bp loop is present downstream of the translational stop codons (nucleotides 5271–5309) and might function as a transcriptional termination signal.

Cleavage of purified SPA protein at methionine residues with CNBr was carried out according to the method of Gross and Witkop (Gross, E. et al; *J. Biol. Chem.;* 237 p.1856–1860; 1962). Fragments were then separated by SDS-PAGE (Schagger, H. et al; *Anal. Biochem.;* 166 p.368–379; 1987), electroblotted onto PVDF paper (Millipore, Milford, Conn.), and stained directly with Coomassie blue. Amino acid sequence analysis was performed on a Model 477A sequencer with Model 120A automated on line PTH analyzer (Applied Biosystems, Foster City, Calif.). N-terminal amino acid sequences of eight CNBr fragments of purified *R. prowazekii* SPA were found within the open reading frame. The DNA sequence predicts the existence of an additional seven CNBr fragments at the carboxy end of the SPA with molecular weights of 0.87 to 8.14 kD. However, despite the fact that all other major CNBr fragments throughout the rest of the molecule were identified, no fragments corresponding to these seven predicted carboxy terminal fragments could be found. A 5.5 kD CNBr fragment beginning at amino acid 1255 (corresponding to nucleic acids 4216–4218) was closest to the putative SPA carboxy terminus.

The open reading frame of pMDL7 encoded a protein with a calculated molecular weight of 169,874 with a theoretical pI of 5.81. Codon usage in the spaP gene is similar to that described previously for the R. prowazekii citrate synthetase gene (Wood, D. O. et al; J. Bacteriol.; 169 p.3564–3572; 1987). The hydrophobicity profile, alpha helical structure, and beta sheet structure (Marck, C.; Nuc. Acids Res.; 16 p.1829–1836; 1988) are plotted in FIG. 3 A, B & C (Theoretical structure analysis of the *R. prowazekii* SPA). Hydropathy (FIG. 3A), alpha helical structure (FIG. 3B), and beta sheet structure (FIG. 3C) are based on the deduced amino acid sequence (DNA Strider, Institut de Recherche Fondamentale). Although most of the protein appears to be largely hydrophobic, the carboxy portion of the molecule appears to be more hydrophilic.

Obviously, many modifications and variations of the present invention are possible in light of the above teachings. It is therefore to be understood that, within the scope of the appended claims, the invention may be practiced otherwise than as specifically described.

What is claimed is:

1. A plasmid consisting of a recombinant DNA insert having the nucleotide sequence of Sequence ID No. 1 (or FIG. 4) which encode the surface layer protein of *R. prowazekii* in a host selected from the group consisting of bacteria, viruses or fungi.

2. The plasmid of claim 1 wherein the host is selected from the group consisting of *Escherichia coli*, attenuated strains of *Salmonella typhi*, *Bacillus Camille - Guerin* (BCG), vaccinia virus, baculovirus expression vectors, and yeast.

* * * * *